United States Patent [19]

Weaver et al.

[11] Patent Number: 4,819,654

[45] Date of Patent: Apr. 11, 1989

[54] METHOD AND APPARATUS FOR DIAGNOSIS OF CORONARY ARTERY DISEASE

[75] Inventors: Charles S. Weaver, Palo Alto; Constance T. Chittenden, Los Altos, both of Calif.

[73] Assignee: SRI International, Menlo Park, Calif.

[21] Appl. No.: 908,604

[22] Filed: Sep. 18, 1986

Related U.S. Application Data

[62] Division of Ser. No. 272,542, Jun. 11, 1981, Pat. No. 4,649,929.

[51] Int. Cl.$^4$ ............................................... A61B 5/02
[52] U.S. Cl. ................................................... 128/680
[58] Field of Search ............... 128/668, 670, 672, 680, 128/681, 682, 683, 687, 688, 695, 696, 700, 707, 713, 715; 364/415, 411

[56] References Cited

U.S. PATENT DOCUMENTS

| | | | |
|---|---|---|---|
| 3,742,936 | 10/1973 | Blanie et al. | 128/713 |
| 3,773,033 | 11/1973 | Rodbard et al. | 128/715 |
| 3,881,481 | 5/1975 | Heule et al. | 128/713 |
| 4,105,021 | 8/1978 | Williams et al. | 128/683 |
| 4,203,451 | 5/1980 | Panico | 128/572 |
| 4,281,663 | 8/1981 | Pringle | 128/707 |

OTHER PUBLICATIONS

Winter et al., "Medical & Biological, Engineering" vol. 11, No. 5, Sep., 1973, pp. 560–568.

Sugira, T. et al., "Noninvasive Assessment of Left Ventricular Performance in Patients With Ischemic Heart Disease: Ear Densitographic Study During Uninterrupted Treadmill Exercise", The American Journal of Cardiology, vol. 48, Jul. 1981, pp. 101–105.

Lewis, R. P. et al., "Usefulness of Systolic Time Intervals in Coronary Artery Disease", The Journal of Cardiology, vol. 37, Apr. 1976, pp. 787–796.

Vanfraechem, J. H. P., "Stroke Volume and Systolic Time Interval Adjustments During Bicycle Exercise". Journal of the American Physiology Society, 1979, pp. 588–592.

Mor, Felix et al., "Relationship Between Systolic Time Interval Measurements and the Extent of Regional Ventricular Asynergy in Coronary Artery Disease", Israel Journal of Medical Sciences, vol. 17, 1981, pp. 1149–1154.

Primary Examiner—William E. Kamm
Attorney, Agent, or Firm—Victor R. Beckman

[57] ABSTRACT

Method and apparatus for recurrently obtaining a measure of the systolic slope of the blood pressure wave in a subject's artery during a range of physical activity, or exercise, are disclosed. A plot, or record, of the slope measurements versus heart beat rate, point in an exercise protocol, or the like, is provided from which subjects having coronary artery disease (CAD) may be distinguished from subjects without CAD.

27 Claims, 7 Drawing Sheets

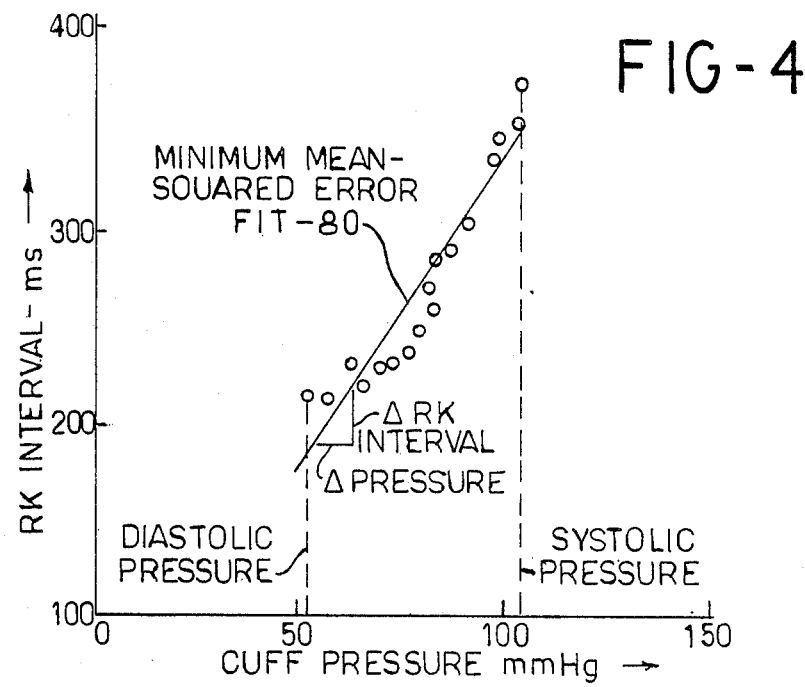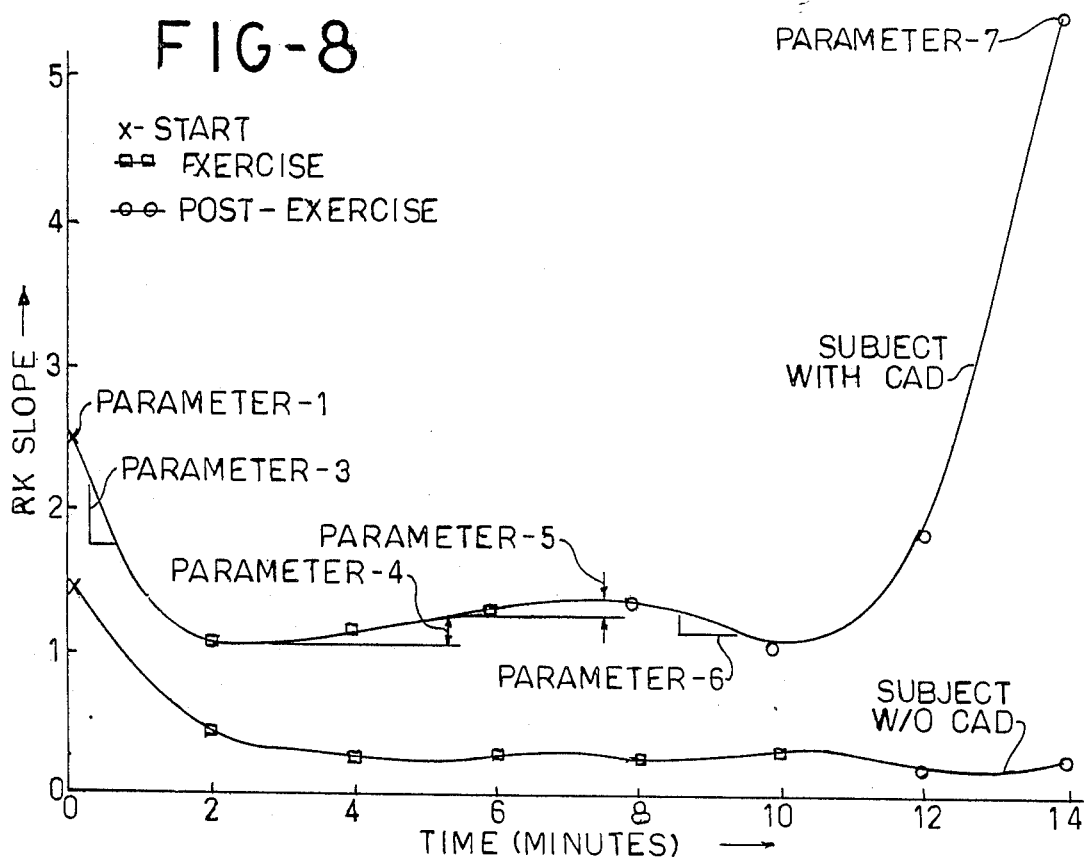

METHOD AND APPARATUS FOR DIAGNOSIS OF CORONARY ARTERY DISEASE

RELATED APPLICATION

This is a divisional of co-pending application Ser. No. 272,542 filed on June 11, 1981, now U.S. Pat. No. 4,649,929.

BACKGROUND OF THE INVENTION

Numerous means for obtaining blood pressure measurements are known including both invasive and noninvasive means. A number of noninvasive measuring means are disclosed in an article by C. S. Weaver, J. S. Eckerley, P. M. Neugard, C. T. Warnke, J. B. Angell, S. C. Terry and J. Robinson, entitled "A Study of Non-invasive Blood Pressure Measurement Techniques" presented at a conference held at Stanford University in September, 1978 and published by the Society of Photo-Optical Instrumentation Engineers.

The use of pulse rate and rhythm measurements as well as measurements of systolic and diastolic blood pressure in the diagnosis of cardiovascular disease has long been known. Electrocardiograph (ECG) measurements also are of well known diagnostic significance in heart disease.

SUMMARY OF THE INVENTION AND OBJECTS

An object of the present invention is the provision of improved diagnostic method and apparatus for the improved diagnosis of coronary artery disease.

An object of the present invention is the provision of improved diagnostic method and apparatus of the above-mentioned type which provides a measure of heart contractility of a subject during a range of exercise.

The above and other objects and advantages of this invention are obtained by recurrently obtaining a measure of the time rate of change in the intra-arterial pressure of a subject during systole (i.e. systolic slope of blood pressure waves in an artery of a subject) before, during and after exercise performed by the subject. Actual values of these measurements at different times in the exercise protocol, as well as certain changes therein during the exercise protocol are determined and compared to corresponding measurements obtained from persons without known CAD for diagnosis of CAD in the subject.

One means for obtaining recurrent measures of the systolic slope of the arterial blood pressure waves includes the use of an inflatable cuff which is inflatable to a pressure above systolic pressure and deflatable to a pressure below diastolic pressure. A pressure transducer is connected to the inflatable cuff for generating a signal which is a function of cuff pressure. A microphone detects Korotkov sounds during deflation of the cuff, and electrodes attached to the subject pick-up electrocardiograph signals. A K-sound detector detects Korotkov sounds from the microphone and an R-wave peak detector detects the peak of the ECG R-wave. The K-sound and R-wave signals from the detectors are converted to signals for use by a computer, and the pressure transducer output is converted to digital form for transfer to the computer and storage in the computer memory. The R-wave and K-sound signals may be supplied as interrupt signals to the computer, with the time of arrival of such signals being stored in the computer memory. Alternatively, ECG and/or Korotkov sound waveforms may be digitized and input to software R-wave and/or K-sound detectors in the computer with the time of arrival of the software detected R-waves and/or K-sounds being stored in the computer memory. The time intervals between the time of arrival of the R-wave signals and the associated K-sound signals during a cuff deflation are determined by the computer and the resultant RK intervals and associated cuff pressures are stored in the computer memory. The RK intervals are processed to discriminate between true Korotkov sounds and artifacts. Using minimum mean-squared fitting techniques, a straight line is fitted by the computer to the collection of true RK interval versus cuff pressure points, which line has a slope inversely proportional to the systolic slope of the arterial blood pressure wave. During a range of exercise a plurality of such "RK-slope" measurements are obtained. These measurements, and changes therein, obtained during an exercise protocol are compared to corresponding measurements and changes therein obtained from healthy subjects for the diagnosis of coronary artery disease (CAD) in the subject.

BRIEF DESCRIPTION OF THE DRAWINGS

The invention will be better understood from the following description when considered with the accompanying drawings. In the drawings, wherein like reference characters refer to the same parts in the several views:

FIG. 4 is a plot of RK interval as a function of cuff pressure for use in explaining the operation of the system shown in FIG. 3;

FIG. 8 shows graphs of measurements of "RK-slope" versus time for a subject with and a subject without coronary artery disease.

Figure 1:
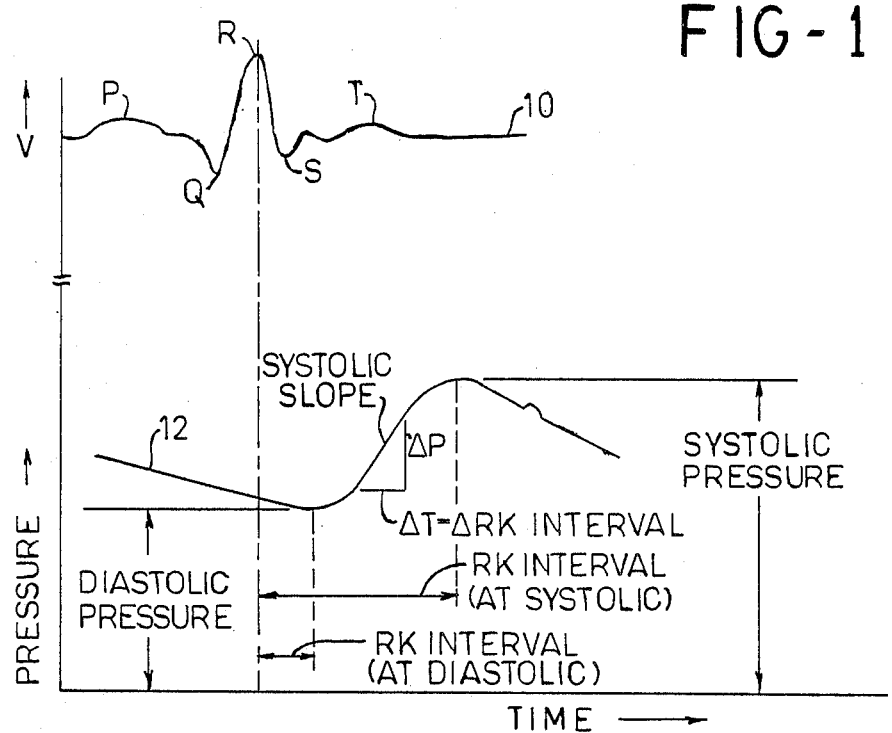
FIG. 1 is a plot of an electrocardiographic signal and an associated arterial blood pressure wave showing RK intervals; measurements of which are made using the system shown in FIG. 3.

Reference first is made to FIG. 1 wherein portions of an electrocardiograph signal 10 and associated brachial artery pressure wave 12 are shown. In accordance with the present invention, recurrent measurements of the systolic slope of the pressure wave are made during an exercise routine. Measurements of the slope together with measurements of certain changes therein which occur during the course of an exercise protocol are evaluated based on corresponding measurements obtained from other subjects with and without known coronary artery disease (CAD) for diagnosis of the disease. Various methods for obtaining a measure of the systolic slope are known in the art, including those described in the abovementioned Weaver et al article. Apparatus of this invention which makes use of one of the slope-measuring methods disclosed in the article is shown in FIG. 3 and described below. First, however, systolic slopes of subjects without CAD and subjects with CAD shown in FIGS. 2A and 2B, respectively, will be described, together with some differences therein useful in the diagnosis of CAD. The systolic slopes depicted in FIG. 2B are representative of many, but not all, types of CAD, and are shown for purposes of illustration only.

Figure 2A:
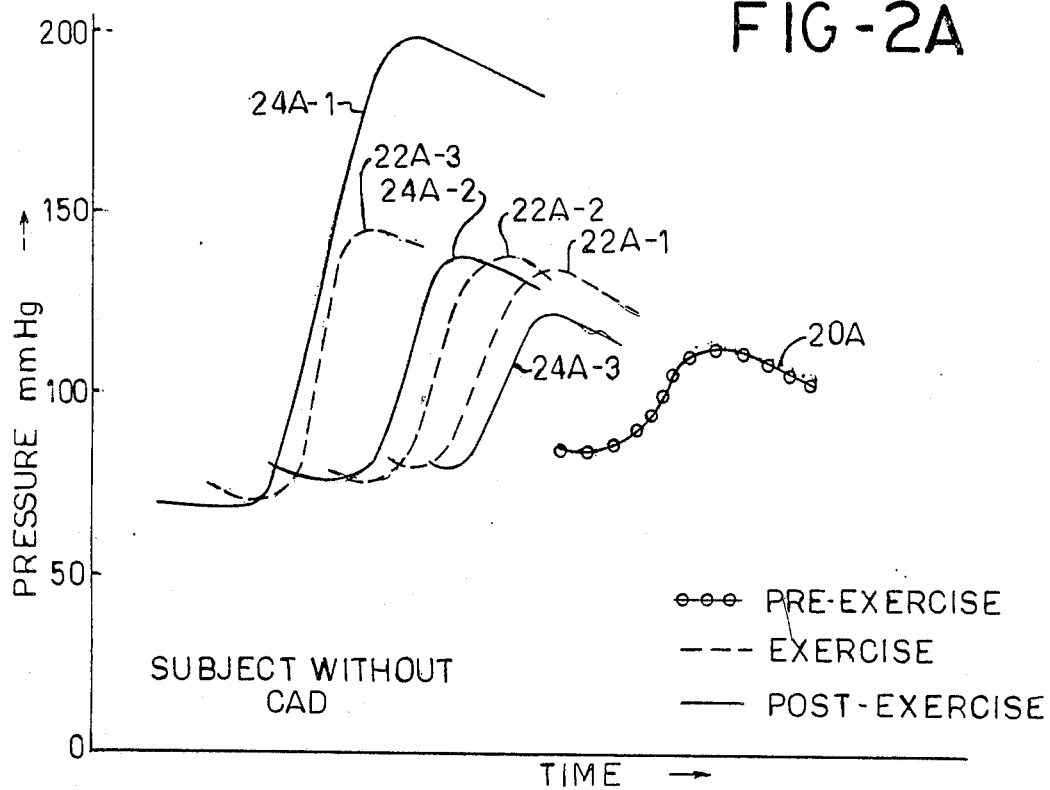
FIGS. 2A and 2B each show graphical representations of arterial blood pressure waves at different times during a range of exercise for subjects without and with, respectively, coronary artery disease.
Figure 2B:
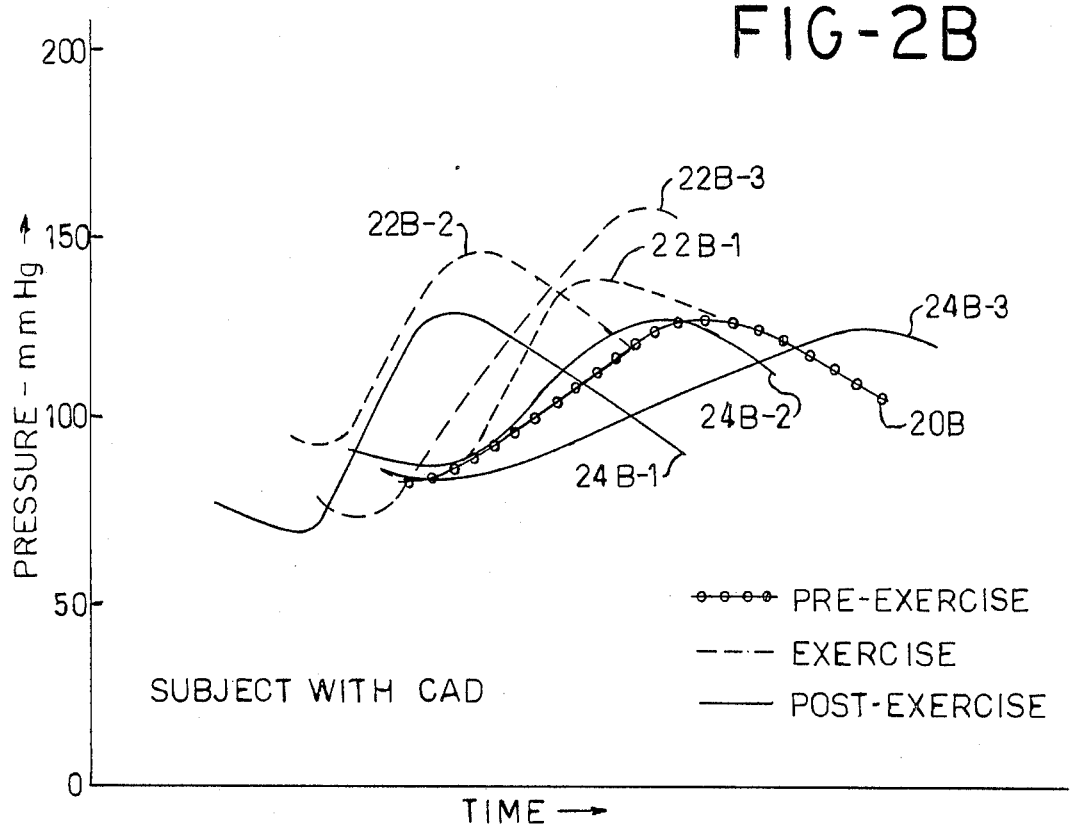
Figure 3:
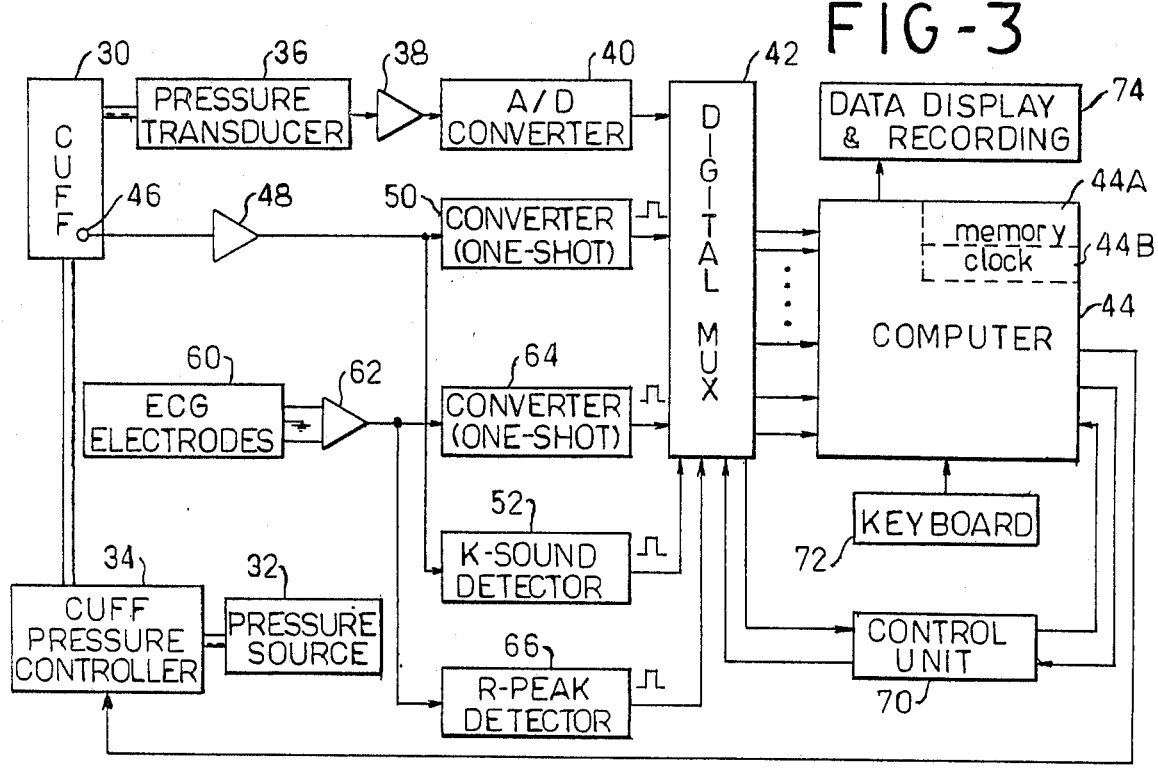
FIG. 3 is a simplified block diagram of a system for recurrently obtaining a measure of the systolic slope of a blood pressure wave and for displaying said measurements, which system embodies the present invention.
Figure 5A:
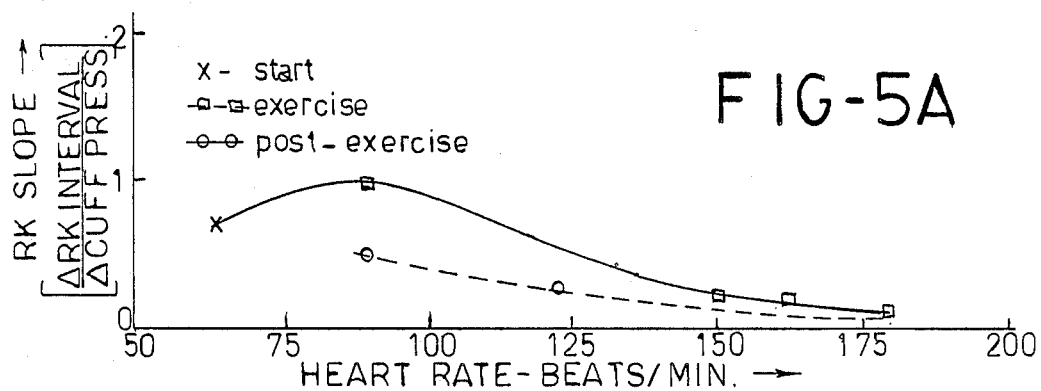
FIGS. 5A-5D are graphs of measurements of slope versus heartbeat rate for subjects with no known coronary artery disease.
Figure 5B:
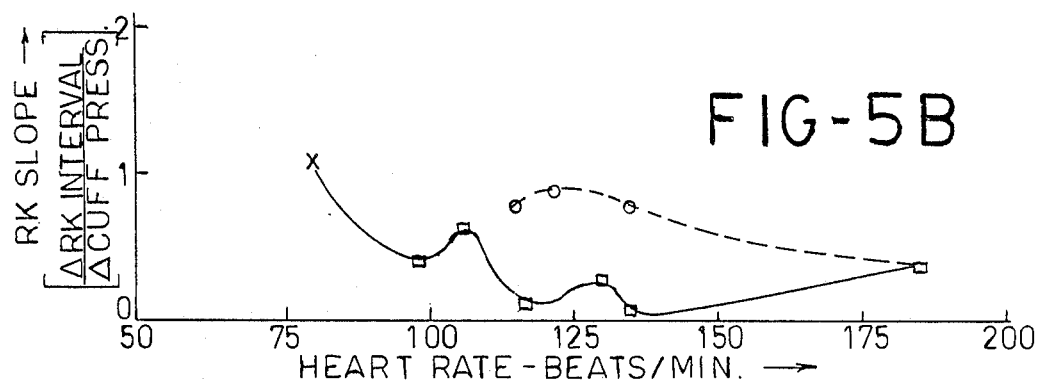
Figure 5C:
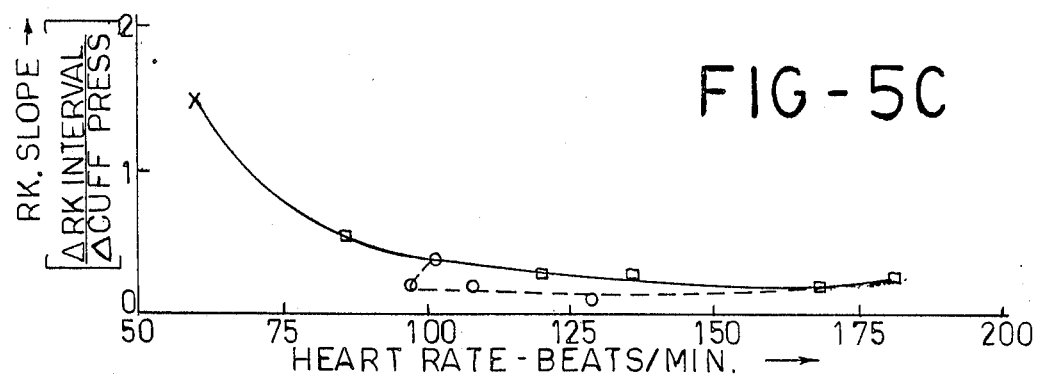
Figure 5D:
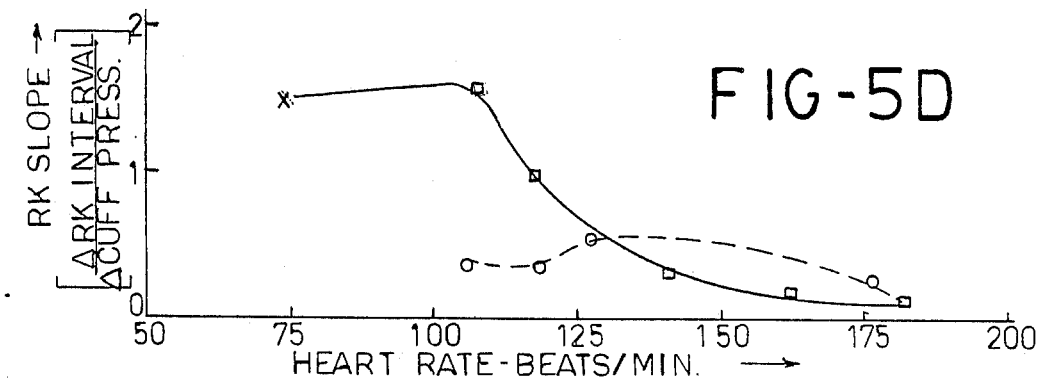

Systolic slope portions of pressure waves obtained before, during and after exercise stress are depicted in FIGS. 2A and 2B. For purposes of description, the same reference characters are used in FIGS. 2A and 2B for pressure pulses obtained at the same relative time during an exercise protocol, except for the use of the suffixes A and B in FIGS. 2A and 2B, respectively. The at rest, before exercise, waves are identified by reference characters 20A and 20B. Both of these waves show systolic and diastolic pressures which are considered to be within normal ranges thereof. The systolic slope of the waves, however, differ, with the systolic slope of pressure wave 20A being greater than that of pressure wave 20B. Typically, the pre-exercise, resting, systolic slope for subjects with CAD is less than that of subjects without CAD.

Pressure waves 22A-1, 22A-2 and 22A-3 shown in FIG. 2A are typical of those observed after 2, 4 and 6 minutes, respectively, of exercise. For the subject without CAD, it will be seen that the systolic slope slowly increases with increasing exercise. Although not seen in FIG. 2A, with increasing exercise the systolic slope generally increases to a maximum value, and remains substantially at said value during continued exercise.

As seen in FIG. 2B, representative pressure waves 24B-1, 24B-2 and 24B-3 during exercise for a subject with CAD show an increase in the systolic slope with exercise, followed by a decrease therein with further exercise. When the left ventricle contracts, not all of the blood is ejected therefrom. Typically, when a subject is at rest, only 50 percent is ejected. The ejection percentage, divided by 100, is the ejection fraction (EF). EF can be measured by injecting a radioactive solution into the blood and then "photographing" the left ventricle with a radionuclide camera at a rate of approximately 30 to 40 photographs per second. These photographs allow the size of the left ventricle to be determined at a number of points during a heart beat, from which determinations of EF can be calculated. Except for a dangerous technique whereby an X-ray dye is injected directly into the coronary arteries, EF measurements during exercise heretofore have provided the most accurate known indicators of CAD. Typically, a healthy subject's EF will gradually increase during exercise, while that of a subject with CAD, first will increase, and then decreases. It is commonly believed that this decrease is due to a decrease in heart contractility. A lower heart contractility lowers the systolic slope of the pressure pulse in the brachial artery. Simultaneous radio-isotope EF and systolic slope measurements have been made on subjects with and without CAD and the above-described correlation between the EF and slope measurements has been observed.

After exercise other differences in the changing systolic slope patterns between healthy subjects and subjects with CAD often are observed, and are illustrated in FIGS. 2A and 2B. Pressure waves 24A-1, 24A-2 and 24A-3 are typical of a healthy subject observed 2, 4 and 6 minutes, respectively, after exercise. Immediately following exercise, the systolic slope remains substantially the same as the slope immediately before the end of exercise, and then slowly decreases with time to the pre-exercise, resting slope. This pattern is in contrast to that observed in many subjects with CAD wherein, after exercise, the systolic slope often decreases beneath the pre-exercise, resting, slope before returning to such pre-exercise slope. Pressure wave 24B-3 in FIG. 2B, at 6 minutes after exercise, is seen to have a systolic slope less than that of the pre-exercise wave 20B. As noted above, such a low systolic slope correlates with low heart contractility and low EF and represents an immediate dangerous physical condition. It here will be noted that although measurements are obtained at corresponding times in the exercise routines for FIGS. 2A and 2B, different effort may be expended by the subjects during the exercise portion of the routines. In FIGS. 5A-5D and 6A-6D plots of measurements of systolic slope as a function of heart beat rate are shown which provide the physician with an indication of the amount of effort exerted by each subject during the exercise routine.

As noted above, various means are known for measuring blood pressure, and the time-derivative of pressure during the systolic slope which provides a measure of the slope. Apparatus for obtaining a measure of the systolic slope of the blood pressure wave embodying the present invention is shown in FIG. 3, to which reference now is made. The illustrated apparatus includes an inflatable cuff 30 for encircling a subject's limb, such as upper arm, and a pressure source 32 connected to the cuff through a pressure controller 34. Cuff pressure is sensed by a pressure transducer 36, the analog output from which is connected through an amplifier 38 to the input of an analog to digital converter 40 for conversion to digital signal form. The digitized cuff pressure signal is connected through a digital multiplexer 42 to a computer 44 which includes memory 44A where cuff pressure signals obtained during a cuff deflation temporarily are stored for use in computing a measure of the systolic slope of blood pressure waves during said deflation.

With the cuff 30 attached to the upper arm of the subject, the cuff is inflated to a pressure above systolic pressure. Then, as the cuff pressure is decreased, the first Korotkov sound appears at the systolic pressure, and the last at the diastolic pressure. A microphone 46 picks up the Korotkov sound (K-sound) at a plurality of cuff pressures between systolic and diastolic. The microphone output signal is amplified by amplifier 48, and the amplifier output is supplied both to a signal converter 50 and to a K-sound detector 52. The converter 50 simply may include a oneshot for generation of a pulse output in response to an amplified K-sound output from amplifier 48, which pulse output is connected to the multiplexer 42. The K-sound detector 52 distinguishes between true K-sounds and artifacts, and produces an output in response to said true K-sounds, which output is connected to an address input of the multiplexer. In the presence of an output from the K- sound detector, the output from the converter 50 is connected through the multiplexer 42 to an interrupt input of the computer 44 to produce a K-sound timing signal which, together with an associated R-wave timing signal, provides a measure of the RK interval.

ECG electrodes 60 attached to the subject's body pick up ECG signals which are amplified by amplifier 62 and then supplied to a converter 64 and to an R-peak detector 66. As with converter 50, the converter 64 also may include a one-shot for generation of a pulse output in response to the R-wave component of the amplified ECG signal. The pulse output from the converter 64 is connected to the multiplexer 42 for connection as an interrupt input to the computer 44. The R-peak detector detects the R-wave of the ECG signal while discriminating against noise and other components, such as the P and T wave components. The R-peak detector output is supplied as an address input to the multiplexer 42 for connection of the output from the converter 64 to an interrupt input of the computer 44 when an R wave is detected. The difference in time between the arrival of an R wave input and associated K-sound signal at the interrupt inputs to the computer provides a measure of the RK interval, which interval is temporarily stored in the computer memory 44A for use with other such RK interval values obtained at different cuff pressures for use in calculating a value related to the systolic slope of the subject's arterial blood pressure wave.

Another address input for the multiplexer 42 is obtained from the computer 44 through a control unit 70. Under control of unit 70, the multiplexer 42 is switched for connection of cuff pressure signals from the A/D converter 40 to the computer 44. Also, multiplexer address input information is supplied to the computer 44 through the control unit 70 for use by the computer in controlling operation of the multiplexer. A keyboard 72 may be included for manual supply of information to the computer, such as the name of the subject to be tested, facts concerning the subject, and various points in the exercise protocol including the start and end of the exercise portion thereof. Data display and recording unit 74 may be used to display and/or record systolic slope information at different exercise levels of the subject. As will become apparent, using the RK interval and cuff pressure information, the computer may be programmed to compute systolic and diastolic blood pressure, which values also may be displayed and/or recorded by unit 74. A system of the type shown in FIG. 3 for measuring systolic and diastolic blood pressure is shown in the above-mentioned Weaver et al article entitled A Study of Non-invasive Blood Pressure Measurement Techniques, the entire disclosure of which article specifically is incorporated by reference herein. However, the relationship between systolic slope as a function of exercise stress and CAD is not disclosed in the article, nor are means for the diagnosis of CAD using measurements of the systolic slope, and changes in the slope, disclosed therein.

Reference again is briefly made to FIG. 1 wherein the relationship between systolic slope of the blood pressure wave 12 and RK interval is shown. The RK interval, i.e. the time interval between the occurrence of the R wave peak and the associated K-sound, is maximum at systolic pressure and minimum at diastolic pressure. As the cuff pressure is decreased from systolic, the RK interval also decreases. As is well understood, the K-sounds are of maximum amplitude intermediate the upper and lower ends of the systolic slope and gradually decrease to zero to systole and diastole.

During cuff deflation, a plurality of RK interval measurements are obtained, and a plot of such measurements as a function of cuff pressure is shown in FIG. 4 to which reference now is made. There, a straight line 80 is shown fitted through the series of points using minimum mean-squared error fitting techniques readily implemented by use of the computer. The slope, $\Delta RK-$ interval/$\Delta$ pressure, of the line is inversely proportional to the systolic slope of the blood pressure wave, as depicted in FIG. 1 and, therefor, provides a measure of the systolic slope of the blood pressure wave. Obviously, as the systolic slope increases, the slope of line 80 decreases, and vice versa. It here will be noted that in the above-mentioned Weaver et al article, the slope of the straight line 80 is determined and utilized in a program for distinguishing between true Korotkov sounds and artifacts. The maximum and minimum cuff pressures at which true Korotkov sounds are obtained provide a measure of the systolic and diastolic blood pressures, respectively, as seen in FIG. 4. The same process disclosed in the Weaver et al article may be used in the present invention to distinguish between true Korotkov sounds and artifacts in order that a true measure of the systolic slope may be obtained. It here will be noted that knowledge of the systolic and diastolic blood pressures is not required in the practice of the present invention. Therefore, in the use of the apparatus of FIG. 3, the slope of the line 80 may be established using only points adjacent the center of the line 80, and not those adjacent the opposite ends thereof where the Korotkov sounds are much weaker. Of course, the apparatus may be used for measuring systolic and diastolic blood pressures, and such pressures may be displayed and/or recorded or stored along with the diastolic slope measurements, if desired. Since the present invention is not specifically directed to the method of distinguishing between true Korotkov sounds and artifacts, it will be understood that such artifacts are removed by suitable processing of the signals from the detector 52, and that points in the plot of FIG. 4 to which the straight line 80 is fitted are obtained using true Korotkov sounds, not artifacts.

For each cuff deflation a series of points are obtained, as shown in FIG. 4, through which the straight line 80 is fitted. The slope of such line is readily calculated by the computer. Using the times of occurrence of the R-peak waves, the time interval between adjacent R-peak waves is determined, and the reciprocal thereof is calculated to provide a measure of heart rate during the cuff deflation. During an exercise cycle, or protocol, the above-described operation is repeated whereby a plurality of values of slope as a function of heart beat measurement, or of time, are obtained, which values may be displayed and/or recorded at display and/or recording unit 74 of FIG. 3. In the present application, the the RK interval versus cuff pressure slope (i.e. slope of line 80 of FIG. 4) is referred to as RK slope, for convenience.

Reference now is made to FIGS. 5A-5D and FIGS. 6A-6D wherein records of the type which may be provided by the present system are shown. In particular, the slope of the straight line fitted to the measured points for each cuff deflation (i.e. RK slope) as a function of heart rate is plotted. Data for these plots of FIGS. 5A-5B was obtained from four healthy subjects having no known CAD while those of FIGS. 6A-6D have CAD. The symbol X marks the point obtained with the subject at rest, before exercise. Points obtained during exercise are identified by the symbol □, and those obtained after exercise are identified by the symbol O. Points for the plots were obtained at two-minute intervals, which intervals may be programmed in the computer 44, or entered through the keyboard 72. It will be understood that substantially continuous measurements may be made, and plotted, there being no requirement for the two-minute spacing between measurements. A clock 44B, shown in FIG. 3, is included to provide time measurements.

Figure 6D:
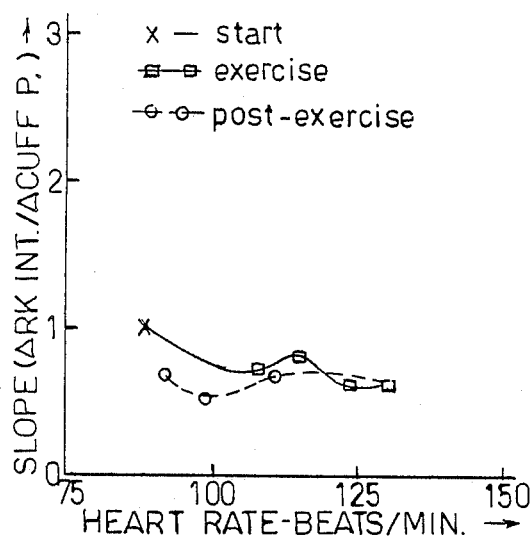
FIGS. 6A-6D are graphs which are similar to those shown in FIGS. 5A-5D for subjects known to have coronary artery disease.
Figure 6C:
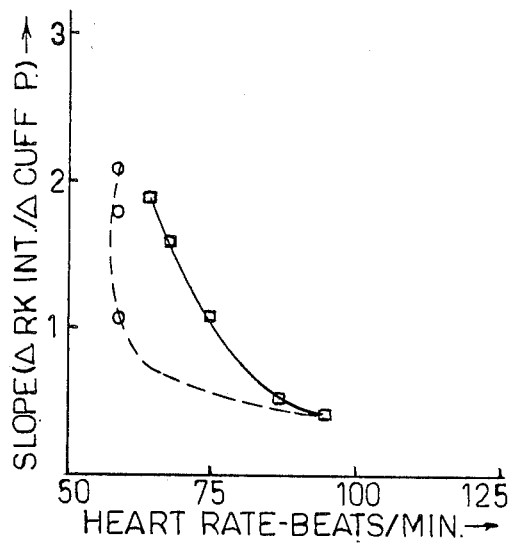
Figure 6A:
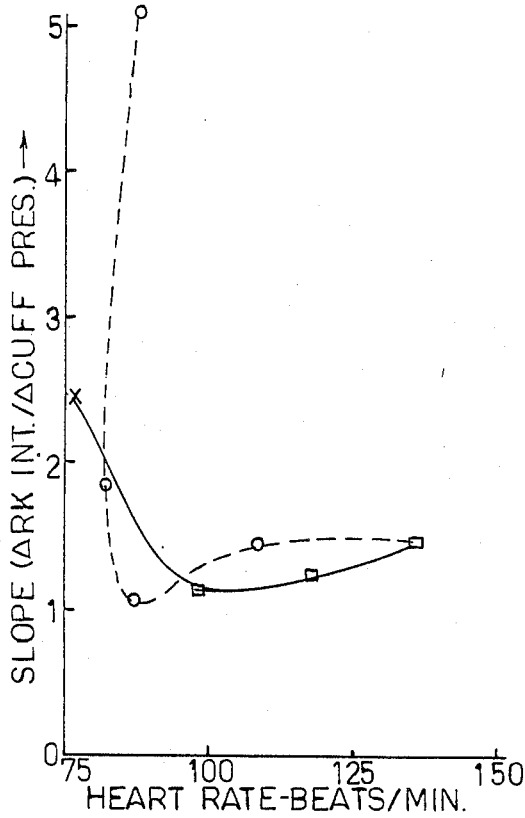
Figure 6B:
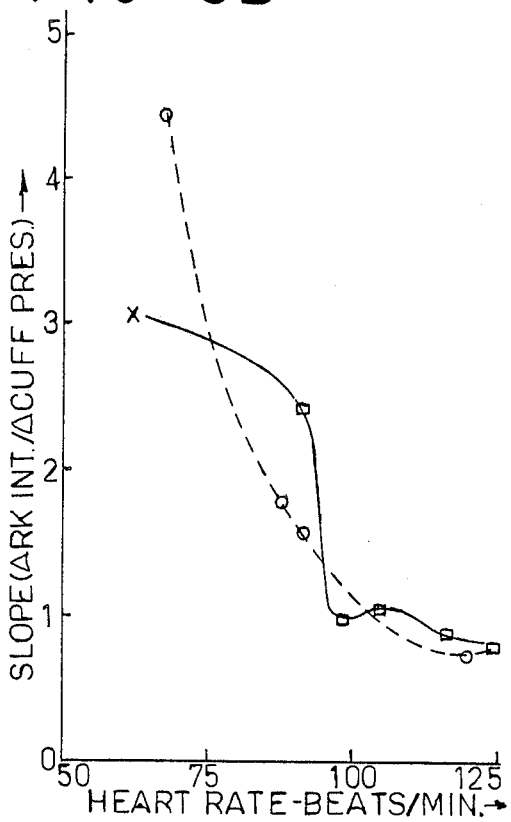

From FIGS. 5A–5D, it will be noted that the RK interval/cuff pressure slope (RK slope) for the four healthy subjects at rest, before exercise, is within the range of approximately 0.6 to 1.5. For subjects with known CAD, the resting slope generally equals or exceeds 2, as seen in FIGS. 6A–6C. Since systolic slope is inversely related to the illustrated slope, it will be seen that the resting systolic slope for a subject with known CAD is generally equal to or less than 0.5. However, in FIG. 6D, the subject with CAD is shown to have a normal starting slope of approximately 1.

During exercise, the RK slope for healthy subjects decreases substantially exponentially to a value slightly above zero, as shown in FIGS. 5A–5D. Since the RK slope is inversely proportional to the systolic slope of the blood pressure wave, this indicates that the systolic slope increases to near-vertical. The undulating nature of the plot of RK slope shown in FIG. 5B during exercise is not typical of healthy subjects.

For CAD subjects, the RK slope also generally decreases during exercise, as seen in FIGS. 6A, 6B and 6C but never reaches levels as low as those reached by healthy subjects. In one CAD case, illustrated in FIG. 6D, there was essentially no change in slope during the entire cycle which too is unlike the change in slope observed in healthy subjects.

After exercise, the RK slope for healthy subjects, shown in FIGS. 5A–5D, slowly returns to the pre-exercise level, while remaining generally within the upper and lower limits reached during exercise. For most subjects with CAD (FIGS. 6A–6C) the slope rapidly rises during the post-exercise period. Often, the post-exercise slope exceeds the pre-exercise slope, as seen in FIGS. 6A–6B, which means that the systolic slope of the brachial artery pulse is low, as is the ejection fraction EF. As mentioned above, in the one CAD case illustrated in FIG. 6D, the post-exercise slope did not significantly change.

Figure 7:
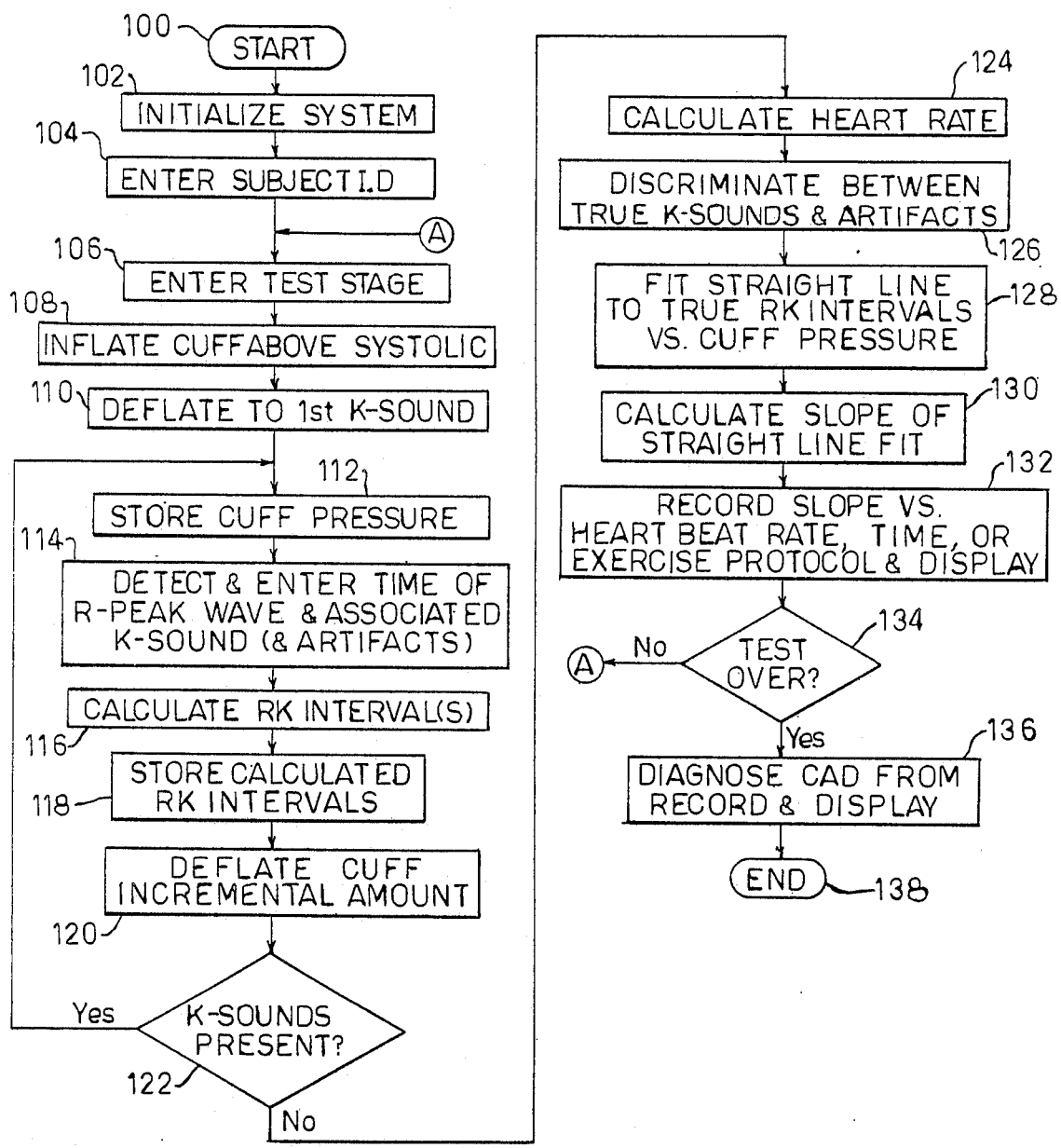
FIG. 7 is a flow chart for use in explaining operation of the system shown in FIG. 3.

Although the operation of the system shown in FIG. 3 for obtaining a measure of the systolic slope during an exercise cycle is believed to be apparent, a brief description thereof with reference to the flow chart of FIG. 7 now will be provided. Various operations indicated therein are under control of the computer 44, responsive to programming instructions contained in memory 44A. Obviously, one or more programming steps may be involved in the actual implementation of the indicated operation. Since the programming of such steps for the indicated operations is well within the skill of the average programmer, a complete program listing is not required and is not included herein.

With the cuff 30 and transducers 46 and 60 properly secured to the subject, the test is started as indicated by START step 100, at which time system power is turned on or a reset operation is performed, by means not shown. Initialization step 102 includes initial setting of counters, registers and the like in the computer 44. Information concerning the subject, such as the subject's name, may be entered through the keyboard 72 at step 104. At step 106, the stage, or portion, of the exercise cycle to be started by the subject is entered by means of the keyboard. For example, at the beginning of the test, the word "pre-exercise" may be entered.

With the subject on a treadmill, stationary bicycle, or the like, cuff inflation step 108 is entered wherein the cuff 30 is inflated under control of the computer to a pressure above systolic blood pressure through operation of the cuff pressure controller 34 to occlude blood flow in the brachial artery. Next, at step 110, the cuff pressure is reduced to a pressure at which true Korotkov, or artifact, sounds are first detected, which, for true Korotkov sounds, is the systolic blood pressure. At this point, the cuff pressure is entered into the computer memory 44A through use of transducer 36, amplifier 38, A/D converter 40 and digital multiplexer 42, as indicated by step 112.

Next, at step 114, an R-peak wave is detected and its time of arrival is entered in the computer memory. The time of arrival of an associated Korotkov sound also is entered into the computer memory. As noted above, in addition to the detection of true Korotkov sounds, the K-sound detector 52 may also respond to artifacts, in which case the time of arrival of such artifacts also is entered into the computer memory. For any given R-peak wave the time of arrival of the true K-sound and that of one or more artifacts may be stored.

At step 116, the RK-interval is calculated, and the RK-interval value, or values, are stored (step 118) with the associated cuff pressure. The cuff pressure, at step 120, is then reduced an incremental amount of, say 4 mmHg. The decision step 122 next is performed to determine whether or not outputs are produced from the K-sound detector 52. If not, it is known that cuff pressure has been reduced beneath diastolic pressure. If the decision is affirmative, i.e. that K-sounds are still being detected, step 112 is again entered, whereupon the new reduced cuff pressure value is stored, together with new associated RK-interval values. When cuff pressure is reduced below diastolic pressure at which time K-sounds no longer are detected, decision step 122 is negative, and step 124 is entered whereupon heart rate is calculated using a count of the R-peak waves. The heart rate is calculated for the preceeding period between cuff inflation and cuff deflation during which a series of RK-intervals at declining cuff pressures is obtained. At step 126, true Korotkov sounds are distinguished from artifacts, and such artifacts are deleted from further processing. In any system, including the present, in which Korotkov sounds are detected, other sounds also are detected by the K-sound detector, particularly when the subject is exercising and such artifacts must be eliminated from the true Korotkov sounds in order to obtain an accurate measure of the systolic slope. As noted above, algorithms for discriminating between true Korotkov sounds and artifacts are included in the above-mentioned Weaver et al article.

Using a minimum mean-squared algorithm, a straight line is fitted to the RK intervals obtained from true Korotkov sounds as indicated at step 128, and the slope of said line is calculated at step 130. At step 132, using the slope calculated at step 130 and heart rate calculated at step 124, a point is recorded on a slope versus heart rate plot (of a type shown in FIGS. 5A–5D and 6A–6D). The decision step 134 then is entered at which point a decision is made as to whether or not the test is to be continued. Keyboard switches, not shown, may be included for manual entry of the decision into the computer 44. If the decision is made to continue the test, step 106 is reentered, at which point the operator, or physician, may enter the next stage in the exercise cycle, such as "exercise". The subject then begins, or continues, that portion of the exercise cycle, and another measure of systolic slope is made and added to the plot. If the test is over, step 136, is entered at which point an analysis is made of the plot by the physician to determine whether or not the plot differs from those of healthy subjects for diagnosis of CAD. The test and diagnosis ends at step 138. It here will be noted that certain steps of the flow chart may be performed in different order.

A number of parameters of, or derived from, the plot of the measure of systolic slope (here, RK-interval/cuff pressure slope) versus heart rate, time, exercise protocol, or the like, may be used for obtaining a value indicative of the subject's heart condition. Pertinent parameters which may be obtained from a plot of RK-slope versus time, include the following, some of which have been described above:

1. Resting RK Slope, prior to exercise,
2. Rate at which the RK slope decreases during a period of time immediately following the start of exercise,
3. Slope of the RK slope versus time plot at the beginning of exercise,
4. Increase in RK slope during exercise,
5. Change in RK slope two minutes after exercise ends,
6. Rate of change in the RK-slope after two minutes after exercise ends, and
7. Highest value of RK slope after exercise.

Typical relative values of the parameters for persons without CAD and persons with CAD are given in table I below wherein the parameter numbers correspond to those in the above list of parameters.

TABLE I

| | Typical Relative Parameter Values | |
|---|---|---|
| Parameter # | Subjects W/O CAD | Subjects with CAD |
| 1 | Low | High |
| 2 | Large | Small |
| 3 | Small | Large |
| 4 | No Increase | Small Increase |
| 5 | Decrease | Increase |
| 6 | Small | Large |
| 7 | Small | Large |

Reference now is made to FIG. 8 wherein a graph, or plot, of measurements of RK slope versus time for a subject without CAD and a subject with CAD are shown, which graph is readily available as an output from the computer. Parameters 1 and 3-7 are identified on the graph of the subject with CAD. It will be noted that the slope of the graph during the first several minutes of exercise changes substantially exponentially for the subject without CAD. On the other hand, the slope of the graph for the subject with CAD during the same initial time period is substantially constant for approximately two minutes, then abruptly decreases. This rate of decrease of the slope is employed in the evaluation of parameter 2.

For each of the parameters, threshold values may be set, or established from an examination of data from a large number of subjects. For example, the threshold for parameter 1, the resting RK-slope prior to exercise, is set between the average for persons with CAD and the average for persons without CAD. From an examination of FIGS. 5A through 5D for healthy subjects the average resting RK-slope before exercise is on the order of 1.2, and from FIGS. 6A through 6D for subjects with known CAD, the average resting slope is on the order of 2.5. A threshold value between these averages of, say 1.8 may be employed. This, and thresholds for the other parameters are stored in the computer memory. For parameter 1, the computed resting RK-slope is compared to the 1.8 threshold value and, if it is less than the threshold it is considered normal. If, as a result of the comparison, the parameter is above the threshold, or cut-point, a value of 1 (one) may be assigned thereto, and if it is below the threshold, a value of $-1$ may be assigned thereto. These outputs are weighted according to the importance of the parameter in the diagnosis; with negative weights being assigned to parameters where necessary. The weighted values for the various parameters simply may be added to provide an overall figure indicative of the condition of the subject's coronary arteries. This figure, together with the individual weighted values may be read out from the computer. Such a system is well adapted for screening large numbers of subjects for CAD.

Figure 9:
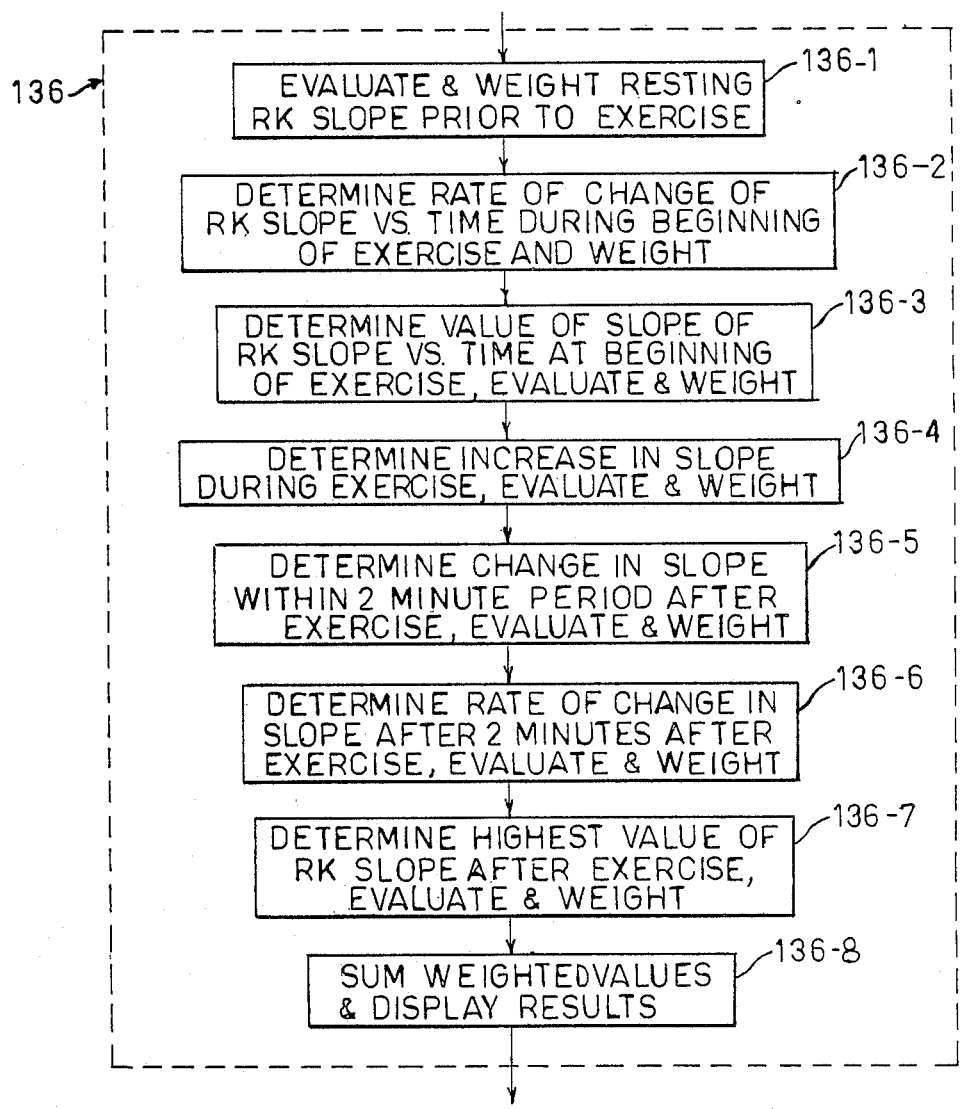
FIG. 9 shows details of a step of the flow chart of FIG. 7 wherein various parameters of the systolic slope measurements are employed by the computer for use in identifying subjects with CAD.

It will be apparent that the parameter values may be obtained directly from the plot or graph of the RK-slope versus time and that manual calculation may be employed in the evaluation. Alternatively, the computer is well adapted for performing such calculations. In FIG. 9, to which reference now is made, details for the block 136 of the FIG. 7 flow chart are shown for computer evaluation of the RK-slope vs time information obtained during an exercise routine of a subject. Parameters 1–7 are determined and/or evaluated and weighted at steps 136-1 through 136-7, respectively, and at step 136-8 the weighted values are summed, and the results are displayed.

It here will be noted that a nonlinear discriminant function which is not suitable for manual analysis also may be included in an algorithm for computer evaluation of measured data.

Of course, the invention is not limited to the above-described algorithmic process. For example, the above-described parameters can be weighted to indicate the relative abnormality of the heart condition. These weighted values may be summed and the total compared to a cut-point for an indication of a normal or an abnormal condition. Again, such an evaluation may be performed manually or by the computer based on the data obtained during the exercise routine.

Heart rate can be substituted for time in the above analyses. All of the parameters except parameter 2 are defined as above. For use with the plot involving heart rate, parameter 2 is defined as the constant c when the function $S(r) = Ke^{-cr}$ is fit to the RK slope versus heart rate data points, where S(r) is the slope, r is the rate, and K is another constant.

The invention having been described in detail in accordance with requirements of the patent statutes, various other changes and modifications will suggest themselves to those skilled in the art. Since the slope of RK interval as a function of cuff pressure is a function of systolic slope, it may be converted to systolic slope which may be plotted as a function of time, heartbeat rate, or the like. Another obvious change includes the use of a manually inflatable cuff rather than the illustrated arrangement wherein cuff inflation and deflation are under control of the computer. Also, as mentioned above and described in the above-mentioned Weaver et al article, systolic and diastolic blood pressure measurements may be obtained from cuff pressure measurements made when true Korotkov sounds are first heard during a cuff deflation, and are last heard, and these pressures also may be displayed and/or recorded. As noted above, the operation of the present apparatus does not depend upon determination of systolic and diastolic blood pressures.

Also, it will be apparent that inputs may be supplied to the computer from the exercise device, or the like, used by the subject whereby the work performed by the subject throughout the exercise cycle may be recorded.

Also, it will be apparent that means other than interrupt inputs may be used to input the time of occurance of the R-peak wave and Korotkov sound to the computer. Either a general purpose or dedicated computer may be employed. Also, a recording of the necessary input may be made, and the recording played back to provide the computer inputs. Additionally, it will be apparent that other blood pressure transducers and systems may be used from which a measure of the systolic slope may be obtained, including, for example, invasive devices. It is intended that the above and other such changes and modifications shall fall within the spirit and scope of the invention defined in the appended claims.

We claim:

1. Apparatus for use in identifying subjects having coronary artery disease comprising,
   an inflatable cuff for encircling a subject's arm,
   means for inflating and deflating said cuff through a range of pressures between systolic pressure and diastolic pressure within which pressure range Korotkov sounds are produced,
   pressure transducer means responsive to cuff pressure and having an output signal related thereto,
   electrode means for sensing electrocardiographic signals from the subject,
   R-wave peak detector means for detecting the peak of the R-wave in the electrocardiographic signals,
   transducer means for sensing Korotkov sounds during a cuff deflation,
   Korotkov sound detecting means for detecting Korotkov sounds in the output from said Korotkov sound transducer means,
   means responsive to the outputs from said pressure transducer, R-wave peak detector, and Korotkov sound detector means for producing a signal representative of the systolic slope of blood pressure waves during a cuff deflation,
   means for recurrently operating said means for producing a signal representative of the systolic slope for obtaining a plurality of said signals representative of systolic slope during different periods of an exercise cycle that includes aerobic exercise performed by the subject,
   means for detecting and evaluating changes in said signals representative of systolic slope occurring during said exercise cycle for identifying subjects having coronary artery disease.

2. Apparatus as defined in claim 1 including display means, and
   means for displaying said signals representative of systolic slope at said display means.

3. Apparatus for use in identifying subjects having coronary artery disease comprising,
   an inflatable cuff for encircling a subject's arm,
   means for inflating and deflating said cuff through a range of pressures between systolic and diastolic pressures within which pressure range Korotkov sounds are produced,
   pressure transducer means responsive to cuff pressure and having an output signal related thereto,
   electrode means for sensing electrocardiographic signals from the subject,
   R-wave peak detector means for detecting the peak of the R-wave in the electrocardiographic signals,
   transducer means for sensing Korotkov sounds during a cuff deflation,
   Korotkov sound detecting means for detecting Korotkov sounds in the output from said Korotkov sound transducer means,
   means responsive to the outputs from said pressure transducer, R-wave peak detector, and Korotkov sound detector means for producing a signal representative of the slope of blood pressure waves during a cuff deflation,
   means for recurrently operating said means for producing a signal representative of the systolic slope for obtaining a plurality of said signals representative of systolic slope during different periods of an exercise cycle that includes aerobic exercise performed by the subject,
   means for determining heart rate of the subject during the exercise cycle,
   display means, and
   means for displaying a plot of said signals representative of systolic slope versus heart rate of the subject at said display means.

4. Apparatus as defined in claim 2 wherein the display provided by said display means includes a plot of said signals representative of systolic slope versus time.

5. Apparatus for use in identifying subjects having coronary artery disease comprising,
   an inflatable cuff for encircling a subject's arm,
   means for inflating and deflating said cuff through a range of pressures between systolic and diastolic pressures within which pressure range Korotkov sounds are produced,
   pressure transducer means responsive to cuff pressure and having an output signal related thereto,
   electrode means for sensing electrocardiographic signals from the subject,
   R-wave peak detector means for detecting the peak of the R-wave in the electrocardiographic signals,
   transducer means for sensing Korotkov sounds during a cuff deflation,
   Korotkov sound detecting means for detecting Korotkov sounds in the output from said Korotkov sound transducer means,
   means responsive to the outputs from said pressure transducer, R-wave peak detector, and Korotkov sound detector means for producing a signal representative of the slope of blood pressure waves during a cuff deflation,
   means for recurrently operating said means for producing a signal representative of the systolic slope for obtaining a plurality of said signals representative of systolic slope during different periods of an exercise cycle that includes aerobic exercise performed by the subject, means for detecting and evaluating changes in said signals representative of systolic slope occurring during said exercise cycle for identifying subjects having coronary artery disease, said means for producing a signal representative of the systolic slope of blood pressure wave including, means for accumulating a plurality of cuff pressure values and associated RK intervals comprising the time between the occurrence of an output from the R-wave peak detector means and the associated Korotkov sound signal from said Korotkov sound detecting means, and means for fitting a straight line to said RK intervals and associated cuff pressure values obtained during a cuff deflation, the slope of which straight line is inversely proportional to the systolic slope of the blood pressure wave.

6. Apparatus as defined in claim 5 including display means, means for determining heart rate of the subject during the exercise cycle, and means for displaying a plot of the slope of said straight line versus heart rate at said display means.

7. Apparatus as defined in claim 1 wherein a systolic slope which increases then decreases during aerobic exercise is evaluated by said evaluating means as being indicative of coronary artery disease in the subject.

8. Apparatus as defined in claim 1 wherein a systolic slope after aerobic exercise which is less than the pre-exercise systolic slope is evaluated by said evaluating means as being indicative of coronary artery disease in the subject.

9. Apparatus as defined in claim 1 wherein a rate of change of systolic slope approximately two minutes after aerobic exercise is terminated which is greater than that for individuals without coronary artery disease is evaluated by said evaluating means as being indicative of coronary artery disease in the subject.

10. Apparatus as defined in claim 1 wherein a rate of change of systolic slope during a period of time immediately following the start of aerobic exercise that is less than that for individuals without coronary artery disease is evaluated by said evaluating means as being indicative of coronary artery disease.

11. Apparatus as defined in claim 1 wherein a systolic slope during the initial portion of the aerobic exercise segment of the exercise cycle is less than that for individuals without coronary artery disease is evaluated by said evaluating means as being indicative of coronary artery disease in the subject.

12. Apparatus as defined in claim 1 wherein a systolic slope after aerobic exercise which is less than that for individuals without coronary artery disease is evaluated by said evaluating means as being indicative of coronary artery disease.

13. A method of screening subjects for coronary artery disease comprising, obtaining a measure of the systolic slope of an artery blood pressure wave of a subject by use of an inflatable cuff with a transducer responsive to cuff pressure, R-wave detecting means, and Korotkov sound detecting means from which transducer and detecting means blood pressure, R-wave and Korotkov sound signals are obtained, respectively, said step of obtaining a measure of the systolic slope including recurrently processing said signals to obtain a signal related to the slope of a straight line fitted to R-wave Korotkov sound intervals versus cuff pressure during cuff deflation between systolic and diastolic blood pressures, which slope related signal provides a measure of systolic slope during said cuff deflation, repeating said step of obtaining a measure of the systolic slope for obtaining a plurality of said measurements over a period of time during which the subject executes an exercise protocol which includes rest before aerobic exercise, aerobic exercise, and rest after aerobic exercise, providing a plot of said measurements, evaluating said plot on the basis of a plurality of different parameters, weighting values obtained from said evaluations, summing the weighted values to obtain a sum, and determining if said sum is outside a predetermined cut-point, a sum outside a predetermined cut-point being used to identify subjects with coronary artery disease.

14. A method as defined in claim 13 wherein the measurement of slope obtained while the subject is at rest prior to exercise comprises one of said plurality of different parameters which is evaluated to obtain a value for weighting.

15. A method as defined in claim 13 wherein said plurality of parameters includes detecting the rate of change of slope measurements during the beginning of the exercise protocol.

16. A method as defined in claim 13 wherein said plurality of parameters includes detecting the slope of said plot at the beginning of the exercise protocol.

17. A method as defined in claim 13 wherein said plurality of parameters includes detecting a change in direction of the measurement of slope during the exercise protocol.

18. A method as defined in claim 13 wherein said plurality of parameters includes detecting the amount of change in the slope measurements during a period of time after exercise during the exercise protocol.

19. A method as defined in claim 13 wherein said plurality of parameters includes detecting the rate of change in the slope measurement occurring during a period of time after exercise during the exercise protocol.

20. A method as defined in claim 13 wherein said plurality of parameters includes detecting the highest value of measurement of slope occurring after exercise during the exercise protocol.

21. Apparatus for use in identifying subjects having coronary artery disease comprising, means for obtaining measurements of the systolic slope of an arterial blood pressure wave of the subject during different periods of an exercise cycle which includes pre-exercise rest, aerobic exercise on a treadmill, stationary bicycle, or the like, and post-exercise rest portions, means responsive to said means for obtaining measurements of the systolic slope for evaluating changes in slope occurring during said exercise cycle for identifying subjects having coronary artery disease.

22. Apparatus as defined in claim 21 wherein a systolic slope which increases then decreases during aerobic exercise is evaluated by said evaluating means as being indicative of coronary artery disease in the subject.

23. Apparatus as defined in claim 21 wherein a systolic slope after aerobic exercise which is less than the pre-exercise systolic slope is evaluated by said evaluating means as being indicative of coronary artery disease in the subject.

24. Apparatus as defined in claim 21 wherein a rate of change of systolic slope approximately two minutes after aerobic exercise is terminated which is greater than that for individuals without coronary artery disease is evaluated by said evaluating means as being indicative of coronary artery disease in the subject.

25. Apparatus as defined in claim 21 wherein a rate of change of systolic slope during a period of time immediately following the start of aerobic exercise that is less than that for individuals without coronary artery disease is evaluated by said evaluating means as being indicative of coronary artery disease.

26. Apparatus as defined in claim 21 wherein a systolic slope during the initial portion of the aerobic exercise segment of the exercise cycle is less than that for individuals without coronary artery disease is evaluated by said evaluating means as being indicative of coronary artery disease in the subject.

27. Apparatus as defined in claim 21 wherein a systolic slope after aerobic exercise which is less than that for individuals without coronary artery disease is evaluated by said evaluating means a being indicative of coronary artery disease.

* * * * *